US006399633B1

(12) United States Patent
Dumont et al.

(10) Patent No.: US 6,399,633 B1
(45) Date of Patent: Jun. 4, 2002

(54) USE OF 4-H-1-BENZOPRYAN-4-ONE DERIVATIVES AS INHIBITORS OF SMOOTH MUSCLE CELL PROLIFERATION

(75) Inventors: Jennifer A. Dumont, Groton, MA (US); Winston Campbell Patterson, Galveston, TX (US)

(73) Assignees: Aventis Pharmaceuticals Inc., Bridgewater, NJ (US); Board of Regents University of Texas System, Austin, TX (US)

( * ) Notice: Subject to any disclaimer, the term of this patent is extended or adjusted under 35 U.S.C. 154(b) by 0 days.

(21) Appl. No.: 09/468,665

(22) Filed: Dec. 21, 1999

Related U.S. Application Data (63) Continuation-in-part of application No. 09/234,380, filed on Feb. 1, 1999, now abandoned.

(51) Int. Cl.[7] ............................................. A61K 31/445
(52) U.S. Cl. ....................................................... 514/320
(58) Field of Search .......................................... 514/320

(56) References Cited

U.S. PATENT DOCUMENTS 4,900,727 A * 2/1990 Kattige et al. ............... 514/212
5,284,856 A * 2/1994 Naik et al. ................... 514/320

FOREIGN PATENT DOCUMENTS

| WO | 9716447 | 5/1997 |
| WO | 9742949 | 11/1997 |
| WO | 9813344 | 4/1998 |
| WO | 9833798 | 8/1998 |

* cited by examiner

Primary Examiner—Raymond Henley, III
(74) Attorney, Agent, or Firm—T. Helen Payne (57) ABSTRACT

The use of 4-H-1-benzopyran-4-one derivatives as inhibitors of smooth muscle cell proliferation. Smooth muscle cell (SMC) proliferation is a critical component of neointimal formation in many animal models of vascular injury, and in many human lesions as well. Cell cycle inhibition by gene transfer techniques can block SMC proliferation and lesion formation in many animal models, although these methods are not yet applicable to the treatment of human disease. Flavopiridol is a recently identified, potent, orally available cyclin-dependent kinase inhibitor. Given the role of smooth muscle cell (SMC) proliferation in vascular disease, we tested the effects of flavopiridol, a recently identified cyclin-dependent kinase inhibitor, on SMC growth in vitro and in vivo. Flavopiridol (75 nmol/L) potently blocked SMC proliferation, an effect that was associated with downregulation of cyclin-dependent kinase activity and cell cycle-related gene expression. We examined the effects of flavopiridol on SMC proliferation in vivo in the rat carotid injury model. Flavopiridol (5 mg/kg) decreased neointimal size by 35% and 39% at 7 and 14 days, respectively, after balloon injury. Flavopiridol may be a potential therapeutic tool in the treatment of SMC-rich vascular lesions. 4-H-1-benzopyran-4-one derivatives inhibit smooth muscle cell proliferation at low dosage levels.

15 Claims, 8 Drawing Sheets

USE OF 4-H-1-BENZOPRYAN-4-ONE DERIVATIVES AS INHIBITORS OF SMOOTH MUSCLE CELL PROLIFERATION

This application is a continuation in part of the prior application bearing U.S. Ser. No. 09/234,380 filed Feb. 1, 1999 now abandoned.

STATEMENT REGARDING FEDERALLY SPONSORED RESEARCH OR DEVELOPMENT

The present invention was made with support from the National Institutes of Health under Grant Nos. HL03658 and AG15234.

FIELD OF THE INVENTION

The instant invention relates to the use of 4-H-1-benzopyran-4-one derivatives as inhibitors of smooth muscle cell (SMC) proliferation.

BACKGROUND OF THE INVENTION

The cellular responses to vascular injury—cellular dysfunction, activation, dedifferentiation, proliferation, and migration—culminate in clinical events such as restenosis, which occurs following balloon angioplasty and stent placement for the treatment of human atherosclerotic disease[1]. Smooth muscle cell (SMC) proliferation is a common, and perhaps unifying, feature of vascular injury models, and SMC are the major cellular component of neointimal lesions[2,3]. Renewed interest in inhibiting SMC proliferation has accompanied the increased use of stents for the treatment of coronary disease, since in-stent restenosis is almost entirely dependent on neointimal formation and SMC hyperplasia[4]. It is estimated that as many as 100,000 patients with in-stent restenosis required treatment in 1997 alone[5]; therefore, an easily administered, effective inhibitor of SMC hyperplasia would have profound clinical and economic ramifications[6].

Efforts to inhibit SMC proliferation in vascular injury models, either by modulating cellular mediators of the proliferative response or by directly interfering with the cell cycle machinery, have provided important insights into neointimal formation. Cell cycle progression is a tightly controlled event regulated positively by cyclin-dependent kinases (Cdks) and their cyclin regulatory subunits[7], and negatively by Cdk inhibitors and tumor suppressor genes such as retinoblastoma protein (Rb) and p53[8]. Adenoviral-mediated overexpression of endogenous Cdk inhibitors p21 and p27$^{kip1}$ or of a constitutively active form of Rb blocks neointimal formation in the rat carotid injury model[9-11]; similarly, inhibition of the activity of transcription factor E2F by competitively overexpressing cognate DNA binding sites also inhibits SMC proliferation and neointimal formation[12]. Such studies support the general hypothesis that cell cycle inhibition is an attractive target for intervention in vascular lesion formation.

Whereas genetic interventions have aided in the dissection of the mechanisms regulating neointimal formation, they suffer from the shortcoming of not being, at present, clinically suitable for the treatment of vascular disease in humans. A water-soluble, low molecular weight compound with specific cell cycle-regulatory effects, particularly one with oral activity, would have broad applicability both experimentally and, potentially, clinically. The recently identified flavone, flavopiridol, is a Cdk inhibitor that potently blocks the activity of $Cdk_2$, $Cdc_2$, and $Cdk_4$[13-16]. In contrast with other pharmacological inhibitors of Cdks, flavopiridol is remarkable for its kinase specificity, its oral availability, and its potency, being effective in nanomolar concentrations[16]. These unique features result in a favorable side effect profile that has led to the testing of flavopiridol in Phase I clinical trials for the treatment of refractory neoplasms[17]. Given these properties, we have examined the ability of flavopiridol to inhibit SMC proliferation in vitro and after balloon injury to the rat carotid artery. We demonstrate that flavopiridol is a potent and selective inhibitor of cell cycle progression and that it arrests SMC proliferation both in vivo and in vitro; moreover, neointimal formation is effectively blocked by oral doses of flavopiridol lower than those known to have toxic effects in humans.

It has now suprisingly been found, that 4-H-1-benzopyran4-one derivatives are suitable SMC proliferation inhibitor. It is know that 4-H-1-benzopyran-4-one derivativesare suitable for controlling tumors. However, it is surprising that 4-H-1-benzopyran-4-one derivatives according to the instant invention effectively act as an SMC proliferation inhibitor at dosage level than the dosage levels which have to be used in the control of tumor growth.

Accordingly, a subject of the instant invention is the use of 4-H-1-benzopyran4-one derivatives as inhibitors of smooth muscle proliferation.

BRIEF DESCRIPTION OF THE DRAWINGS

FIG. 1. Effect of flavopiridol on HASMC DNA synthesis. A. Quiescent HASMC were treated in the absence (−) or presence (+) of bFGF (10 ng/ml) and with the indicated concentrations of flavopiridol (nmol/L) for 24 h. BrdU incorporation as a measure of proliferation was determined by an ELISA-based assay and expressed as percentage of incorporation in the absence of bFGF treatment. *$p<0.05$, compared to untreated cells. †$p<0.05$, compared to treatment with bFGF in the absence of flavopiridol. B. HASMC were treated with bFGF (10 ng/ml), thrombin (2 U/ml), or vehicle in the presence of absence of flavopiridol (75 nmol/L) and BrdU incorporation was measured. *$p<0.05$, compared to untreated cells. **$p<0.05$, compared to treatment with bFGF alone. †$p<0.05$, compared to treatment with thrombin alone.

FIG. 2. Effect of flavopiridol on HASMC proliferation. Quiescent HASMC were treated with bFGF (10 ng/ml) alone (□), bFGF and flavopiridol (75 nmol/L) (□), or vehicle (□) for the times indicated and cell numbers after treatment were determined. Results are expressed as the cell counts per well ($\times 10^3$).

FIG. 3. Effect of flavopiridol on cyclin-dependent kinase activity in HASMC. Quiescent HASMC were treated with bFGF (10 ng/ml), thrombin (2 U/ml), or vehicle in the presence or absence of flavopiridol (75 nmol/L), and phosphorylation of histone H1 was quantified as a measure of Cdk activity and expressed as a percentage of Cdk activity in the absence of bFGF treatment. *$p<0.05$, compared to untreated cells. **$p<0.05$, compared to treatment with bFGF alone. †$p<0.05$, compared to treatment with thrombin alone.

FIG. 4. Regulation of cell cycle-related proteins by flavopiridol. Quiescent HASMC were treated in the presence (+) or absence (−) of bFGF (10 ng/ml), thrombin (2 U/ml), and/or flavopiridol (75 nmol/L) for 24 h. Immunoblotting of cellular lysates was performed with specific antibodies recognizing cyclin $D_1$ (top panel), PCNA (middle panel), and phosphorylated (pRb) and hyperphosphorylated (ppRb) Rb (lower panel).

FIG. 5. Effects of flavopiridol on MAP kinase activity in HASMC. Quiescent HASMC were treated in the presence (+) or absence (−) of bFGF (10 ng/ml), thrombin (2 U/ml), PD98059 (30 μmol/L) and/or flavopiridol (75 nmol/L) for 30 min. Levels of phosphorylated Erk1 (pErk1) and Erk2 (pErk2) were measured by immunoblotting with a phosphorylation-specific antibody recognizing both proteins (upper panel). MAP kinase activity was measured with an in-gel kinase assay, using myelin basic protein as a substrate (lower panel).

FIG. 7. Inhibition of rat carotid artery neointimal formation by flavopiridol after balloon injury. Neointima/media ratios were measured in histologic sections or rat carotid arteries treated with or without flavopiridol (5 mg/kg) for 5 days after injury. Arteries were examined 7 (n=12) and 14 (n=12) days after injury. The percentage of PCNA-positive nuclei (±SEM, expressed as a percentage of counted nuclei) in the neointima of arteries from each time point and treatment group is also given. *p<0.05 compared to treatment with vehicle.

FIG. 9. Cdk2 expression after balloon injury in rat carotid arteries. Sections are from arteries 7 (panels A and B) and 14 (panels C and D) days after injury. The arteries shown in panels A and C were from rats treated with flavopiridol (5 mg/kg) by gavage; the arteries in panels B and D were from rats treated with vehicle alone. Cdk2-positive nuclei, located predominantly in the neointima, are stained with Vector blue by the alkaline phosphatase method. Original magnification, ×100.

Suitable 4-H-1-benzopyran are compounds of the formula

Formula I wherein $R_1$ is hydrogen, alkyl having 1 to 6 carbon atoms, aryl-$C_1$–$C_4$-alkyl; $C_1$–$C_6$-alkyl substituted by halogen, hydroxy, or carboxy; $C_3$–$C_6$-cycloalkyl, pyridyl, thienyl, $C_3$–$C_6$-cycloalkyl-$C_1$–$C_4$-alkyl, $C_2$–$C_6$-alkenyl, $C_2$–$C6$-alkynyl, phenyl; phenyl, mono- or polysubstituted by halogen, $C_1$–$C_4$-alkyl, $C_1$–$C_4$-alkoxy, hydroxyl, carboxyl, COO-alkyl, $CONH_2$, CONH-alkyl, CON(alkyl)$_2$, nitro, trifluoromethyl, amino, $C_1$–$C_4$-alkylamino, di-$C_1$–$C_4$-alkylamino, or phenyl; naphthyl, carboxyl, —CHO, COO—$C_1$–$C_4$-alkyl, a primary amino, alkylamino, aralkylamino, dialkylamino, amido, arylamino, diarylamino, or —CH$_2$O—$C_1$–$C_4$-alkyl;

$R_2$ is hydrogen, alkyl having 1 to 6 carbon atoms, aryl, nitro, amino, di-$C_1$–$C_4$-alkylamino, a halogen, hydroxyl, alkoxy, —COOH, —COO—$C_1$–$C_4$-alkyl, —CHO, —CH$_2$OH or —CH$_2$O—$C_1$–$C_4$ alkyl;

$R_3$ is hydrogen, $C_1$–$C_4$-alkyl; $C_1$–$C_4$-alkyl substituted by halogen, hydroxy or carboxy; hydroxyl, carboxyl, nitro, amino, $C_1$–$C_4$-alkylamino, di-$C_1$–$C_4$-alkylamino, halogen, —O-alkyl-C(O)-alkyl, —CHO, —CH$_2$OH, —CH$_2$O-$C_1$–$C_4$-alkyl or $R_2$N—C(O)—O—, wherein R is H, $C_1$–$C_6$-alkyl, cycloalkyl; or —O-alkyl-C(O)-alkyl or aryl;

$R_4$ is hydrogen, hydroxyl, $C_1$–$C_4$-alkoxy, $C_1$–$C_4$-alkanoyloxy, $C_1$–$C_4$-alkoxycarbonyl, aryloxy, amino, $C_1$–$C_4$-alkylamino, di-$C_1$–$C_4$-alkylamino, or R'$_2$-N—C(O)—O—wherein R' is H, $C_1$–$C_6$-alkyl, cycloalkyl or aryl;

$R_5$ is hydrogen, $C_1$–$C_6$-alkyl, aryl-$C_1$–$C_4$ alkyl, $C_3$–$C_6$-cycloalkyl, $C_3$–$C_6$-cycloalkyl-$C_1$–$C_4$-alkyl, alkyl amino, $C_1$–$C_4$-alkanoyl, —C(O)—O-$C_1$–$C_4$-alkyl or aroyl, where the aryl group in $R_1$, $R_2$, $R_3$, $R_4$, and $R_5$ is unsubstituted phenyl or phenyl that is mono or polysubstituted by halogen, $C_1$–$C_4$-alkyl, $C_1$–$C_4$-alkoxy, hydroxyl, carboxyl, COO-alkyl, $CONH_2$, CONH-alkyl, CON(alkyl)$_2$, nitro, trifluoromethyl, amino, $C_1$–$C_4$-alkylamino, di-$C_1$–$C_4$-alkylamino or phenyl;

m is an integer between 0 and 3 and n is 1, or a pharmacologically acceptable acid addition salt thereof.

The compounds according to the invention have two centers of asymmetry, one where the heterocyclic ring containing nitrogen is fused to the benzopyran moiety (C-4'), the other at the $R_4$-substituted carbon atom (C-3'), which means that two pairs of optical isomers are possible. The definition of the compounds according to the invention embraces all possible stereoisomers and their mixtures. It very particularly embraces the racemic forms and the isolated optical isomers having the specified activity. The two racemates can be resolved by physical methods, such as, for example, fractional crystallization. The individual optical isomers can be obtained from the racemates by conventional methods, such as, for example. salt formation with an optically active acid followed by crystallization.

Examples of alkyl groups which are suitable for $R_1$ to $R_5$ are straight-chain or branched radicals having up to 6, preferably up to 5, carbon atoms, for example methyl, ethyl, propyl, isopropyl, t-butyl, pentyl or isopentyl groups.

Examples of substituted alkyl groups which are suitable for $R_1$ to $R_5$ are haloalkyl, such as trifluoromethyl, hydroxyalkyl, such as hydroxyethyl, or carboxyalkyl, such as carboxyethyl.

Suitable examples of a cycloalkyl group which has 3 to 6 carbon atoms and is represented by $R_1$ to $R_5$ are cyclopropyl, cyclobutyl, cyclopentyl or cyclohexyl. Cyclopropylmethyl is an example of cycloalkylalkyl.

An example of an aralkyl group which is represented by $R_1$ to $R_5$ is a phenylalkyl group in which the phenyl group is unsubstituted or monosubstituted or polysubstituted by substituents such as halogen, $C_1$–$C_4$-alkyl, $C_1$–$C_4$-alkoxy or nitro or by a trifluoromethyl group, amino group and substituted amino group.

An example of an aryl group which is represented by $R_1$ to $R_5$ is a phenyl group which is unsubstituted or monosubstituted or polysubstituted by substituents such as halogen, $C_1$–$C_4$-alkyl, $C_1$–$C_4$-alkoxy, hydroxyl, carboxyl, COO-alkyl, $CONH_2$, CONH-alkyl, $CON(alkyl)_2$, nitro or trifluoromethyl, amino, $C_1$–$C_4$-alkylamino, di-$C_1$–$C_4$-alkylamino, aromatic heterocyclic groups such as pyridyl groups, and polycyclic aromatic radicals, such as naphthyl groups.

A suitable example of an alkylamino group which is represented by $R_1$ to $R_5$ is $(CH_2)_n$—$NR_6R_7$, where n is 1 to 3 and $R_6$ and $R_7$ are alkyl and are as defined as above in the case of alkyl $R_1$ to $R_5$; moreover, $R_6$ and $R_7$ together with the nitrogen atom to which they are bonded can be a heterocyclic ring having one or more hetero atoms. Suitable examples of heterocyclic rings which are formed by $R_6$ and $R_7$ together with the nitrogen to which they are bonded are piperidine. pyrrolidine, morpholine, piperazine or imidazole, all of which can be unsubstituted or substituted in one or more positions by $C_1$–$C_4$-alkyl, $C_1$–$C_4$-alkoxy or aryl or by a hydroxyl or amino group.

Suitable examples of salts of the compounds according to the invention with inorganic or organic acids are hydrochloride, hydrobromide, sulfate, phosphate, acetate, oxalate, tartrate, citrate, maleate or fumarate.

Preferred are compounds of the formula Ia

Formula Ia in which $R_1$ is hydrogen, $C_1$–$C_3$-alkyl, naphthyl, phenyl; phenyl mono- or polysubstituted by halogen, $C_1$–$C_4$-alkyl, $C_1$–$C_4$-alkoxy, hydroxyl, carboxyl, COO-alkyl, $CONH_2$, CONH-alkyl, $CON(alkyl)_2$, nitro, trifluoromethyl, amino, $C_1$–$C_4$-alkylamino, di-$C_1$–$C_4$-alkylamino, or phenyl; pyridyl, or thienyl;

$R_2$ is hydrogen or $C_1$–$C_3$-alkyl;

$R_5$ is $C_1$–$C_3$-alkyl, $C_3$–$C_5$-cycloalkyl, or $C_3$–$C_5$-cycloalkyl-$C_1$–$C_4$-alkyl.

Particularly preferred are compounds of formula Ia, in which $R_1$ is phenyl, thienyl, pyridyl, chlorophenyl, dichlorophenyl, methylphenyl, aminophenyl, bromophenyl, hydroxyphenyl or naphthyl;

$R_2$ is hydrogen and $R_5$ is methyl.

A compound of special importance is (–)-cis,-5,7-dihydroxy-2-)(2-chlorophenyl)-8-[4-(3-hydroxy-1-methyl)-piperidinyl]-4H-benzopyran-4-one (Flavopiridol), particularly in the form of hydrochloride.

The compounds according to the instant invention can be prepared according to the disclosure of U.S. Pat. No. 4,900,727 and U.S. Pat. No. 5,284,856 which are incorporated herein by reference. The examples of said U.S. patents are also of relevance for the instant application.

The compounds according to the instant invention inhibit smooth muscle cell proliferation. Further subject-matter of the invention are therefore also pharmaceuticals for the inhibition of smooth muscle cell proliferation, which contain at least one compound of the formula I as defined above or at least one of its pharmacologically acceptable acid addition salts, and the use of a compound of the formula I as defined above for the preparation of a pharmaceutical having an smooth muscle cell proliferation inhibitory action. Typical application areas for the compounds according to the instant invention are diseases/disorders/injuries which are accompanied by smooth muscle cell-rich vascular lesions. A very important example therefor are lesions after balloon injury. Another important application area is the prevention of restenosis after stent implantation.

The 4H-1-benzopyran-4-one derivatives are used according to the invention in the generally known fashion which is known to the expert. For pharmaceuticals, an effective amount of the active substance mentioned is employed either per se or preferably in combination with suitable pharmaceutical auxiliaries in the form of tablets, coated tablets, capsules, suppositories, emulsions, suspensions or solutions, the active compound content being up to about 95%, preferably between 10 and 75%.

The expert will know which auxiliaries are suitable for the desired formulation of the pharmaceutical because of his expert knowledge. Besides auxiliaries for tablets, or solvents, gel formers, bases for suppositories and other excipients for the active substance, it is possible to use, for example, antioxidants, dispersants, emulsifiers, defoamers, flavor corrigants, preservatives, solubilizers or colorants.

The active substance can be administered orally, parentally, intravenously or rectally, oral administration being preferred. For a form of oral administration, the active substance may be mixed with other compounds together with the additives which are suitable for this purpose, such as excipients, stabilizers or inert diluents, and customary methods can be used for bringing it into suitable administration forms, such as tablets, coated tablets, hard-gelatin capsules, and aqueous alcoholic or oily suspensions or solutions. Examples of inert excipients which can be used are gum arabic, magnesia, lactose, glucose or starch, in particular corn starch. In this context, the formulation can be prepared as dry granules or moist granules. Examples of suitable oily excipients or solvents are vegetable or animal oils, such as sunflower oil or cod-liver oil.

For subcutaneous or intravenous administration, a solution, suspension or emulsion of the active substance is formed, if appropriate using substances which are conventional for this purpose, such as solubilizers, emulsifiers or other auxiliaries. Examples of suitable solvents are water, physiological sodium chloride solution or alcohols, for example, ethanol, propanol or glycerol, and also sugar solutions, such as glucose solutions or mannitol solutions, or a mixture of the various solvents which have been mentioned.

The dose of 4H-1-benzopyran-4-one derivatives which is to be administered daily is to be selected to suit the desired effect. The 4H-1-benzopyran-4-one derivatives can be administered in a dose which is less than 70%, preferably less that 60%, in particular less than 50% of the dosage, which is used to control tumor growth in the respective mammal. An example would be—in a nude mouse xenograft model—a dose of about 5 mg/kg bodyweight administered orally once daily. This is half of the dosage which inhibits tumor growth in the same animal model (Drees et al. Clin. Cancer Res. 1997; 3: 273–279).

The pharmacokinetic properties of the 4H-1-benzopyran-4-one derivatives could make it necessary to administer the said compound several times a day or to chose slow release formulations.

EXAMPLES

1. Flavopiridol inhibits smooth muscle cell proliferation and neointimal formation in vivo in a rat carotid injury model of vascular injury.

The well-established rat carotid injury model, in which neointimal lesion formation after catheter-induced injury is critically dependent on SMC proliferation (Clowes et al. Lab. Invest. 1983; 49:327–333, Clowes et al. Circ. Res. 1985; 56:139–145) to examine whether Flavopiridol induces growth arrest of SMC in vivo, as it does in vitro. Flavopiridol was administered orally at a dose of 5 mg/kg once daily, beginning on the day of injury and for four days after, since this time period covers the initial induction of Cdk2 and the first wave of SMC proliferation in this model (Circ. Res.1995; 77:445–465, Circ. Res.1997; 80:418–426). Mean intimal and medial areas were quantified 7 and 14 days after injury, and neointimal lesion size was expressed as the ratio of the neointimal to the medial area. Twelve animals each were in the treated and untreated groups. The ratio at 7 days was 1.00+/−0.05 in arteries of vehicle-treated rats and 0.65+/−0.04 in Flavopiridol-treated rat arteries, a reduction of 35%. At 14 days, the neointimal/media ratio was 1.08+/−0.04 in vehicle-treated rats and 0,66+/−0.03 In Flavopiridol-treated rats, a reduction of 38.9%. These effects were statistically significant at both time points (P<0,05).

Methods

Materials—Flavopiridol (L86-8275, (−)-cis, -5,7-dihydroxy-2-(2-chlorophenyl)-8-[4-(3-hydroxy-1-methyl) piperidinyl]-4H-benzopyran-4-one) was provided by Hoechst Marion Roussel, Inc., and was dissolved in dimethyl sulfoxide as a stock solution of 50 mmol/L for cell culture experiments or in water for in vivo experiments. Basic fibroblast growth factor (bFGF) was purchased from Collaborative Biochemical and thrombin from Sigma. The MEK1 inhibitor PD98059 was obtained from New England Biolabs.

Cell culture—Human aortic smooth muscle cells (HASMC) were obtained from Clonetics and were cultured as previously described[18]. Cells were used at passages 5–9. Prior to performing experiments, cells were growth-arrested at 80% confluence for 48 h with medium containing 0.2% fetal bovine serum.

Cell proliferation ELISA—Cell proliferation was measured by ELISA (Amersham Life Science). HASMC were grown in gelatin-coated 96-well plates and made quiescent. Cells were treated with 10 ng/ml bFGF, 2 U/ml thrombin, or vehicle for 24 h. Flavopiridol (75 nmol/L) was administered 1 h prior to growth factor treatment. 5-Bromo-2′-deoxyuridine (BrdU) was added to a final concentration of 10 $\mu$mol/L during the last 2 h of treatment. BrdU incorporation was measured as described[19]. Results are expressed as mean±SEM for 12 samples per condition from two independent experiments.

Cell counts—Growth-arrested HASMC grown to 50% confluence in 6-well plates were treated with or without flavopiridol (75 nmol/L) or bFGF (10 ng/ml). At intervals after treatment, cells were trypsinized and cell numbers determined using a hemocytometer.

Western blot analysis—Quiescent HASMC were treated in the presence or absence of growth factors and/or flavopiridol as indicated. Western blot analysis was performed as previously described[18]. The primary antibodies were: a polyclonal anti-human cyclin D1 antibody (M-20, Santa Cruz), a monoclonal anti-human proliferating cell nuclear antigen (PCNA) antibody (PC10, Sigma), a phosphorylation-specific p44/42 (Erk1/Erk2) MAP kinase monoclonal antibody (New England Biolabs), and a monoclonal anti-Rb antibody (G3-245, Pharmigen), which recognizes the phosphorylated (pRb) and highly phosphorylated (ppRb) Rb species. For immunoblotting studies, experiments were repeated at least three times.

Cdk activity—Quiescent HASMC were treated with agonists and inhibitors for 24 h and total cell lysates were prepared as described for Western blotting. The kinase assay was performed with a histone $H_1$ kinase assay kit (Upstate Biotechnology) following the manufacturer's instructions. In brief, 10 $\mu$l of peptide inhibitors for protein kinase C (2 $\mu$mol/L) and protein kinase A (2 $\mu$mol/L), 100 $\mu$g cell lysate, 10 $\mu$l assay buffer and 10 $\mu$l of a mixture containing 75 $\mu$mol/L magnesium chloride, 500 $\mu$mol/L ATP and 1 $\mu$Ci/ml [$\gamma$-$^{32}$P]ATP were mixed in a microcentrifuge tube. After incubation at 30° C. for 10 min, aliquots were pipetted onto phosphocellulose papers. The papers were washed in 0.75% phosphoric acid, followed by measurement of cpm in a scintillation counter (Beckman). Results are expressed as the mean±SEM for three samples and are representative of three independent experiments.

In-gel kinase assay—Quiescent HASMC were treated with growth factors for 30 min and total cell lysates were prepared as described for Western blotting. In some experiments, HASMC were pretreated for 60 min with 30 $\mu$mol/L PD98059, flavopiridol, or vehicle. Equal amounts of proteins (50 $\mu$g/lane) were resolved on a polyacrylamide gel that was copolymerized with 350 $\mu$g/ml myelin basic protein. The gel was treated with [$\gamma$-$^{32}$P]ATP and autoradiography was performed as described[19].

Trypan-blue exclusion—HASMC were grown in 5-cm dishes at low confluence and growth-arrested as described. Cells were treated with flavopiridol (75 nmol/L) or tumor necrosis factor-□ (TNF-□; 50 ng/ml) for the indicated times. Following the removal of the medium, 0.4% trypan blue in phosphate-buffered saline was added to the dishes. After 5 min, the cells in the dishes were counted under the microscope. Blue cells were counted as nonviable cells.

Rat carotid injury model—Injury to the rat carotid artery was performed essentially as described[2]. Adult male Sprague-Dawley rats (400–500 g, Zivic-Miller) were anesthetized with an intraperitoneal injection of ketamine (2 mg/kg) and xylazine (4 mg/kg). The left internal carotid was then cannulated with a 2F embolectomy catheter. The balloon was inflated with saline and withdrawn across the artery three times to produce a distending and denuding injury. The right carotid artery was uninjured and served as a control of injury for each animal. Immediately following recovery from anesthesia and for four additional days thereafter, rats were administered flavopiridol (5 mg/kg in water) or water by gavage in a blinded manner. All rats survived the surgery and there were no overt signs of toxicity related to drug administration in the doses used. At specified time points after carotid injury, rats were anesthetized as above and perfusion-fixed systemically with 4% paraformaldehyde in phosphate-buffered saline. Right and left carotid arteries were removed and distended by injection of 4% paraformaldehyde through the lumen, after which they were dehydrated and stored in 70% ethanol at 4° C. Immunohistochemistry was performed as previously described[18], using the monoclonal PCNA antibody and a polyclonal anti-human Cdk2 antibody (M2-G, Santa Cruz).

Image analysis—The extreme distal and proximal regions of each artery (approx. 500 $\mu$m) were removed. Ten intermediate cross-sections (8 μm each) taken 500 μm apart were analyzed from each artery. Slides were fixed and stained with hematoxylin and eosin as previously described[18]. Using a Nikon Diaphot 300 microscope and a 4× objective, each cross-section was captured as a digital image using a Hamamatsu C5985 video camera and TCPro 2.41 (Coreco, Inc.). Medial and neointimal areas were determined using NIH Image software. Medial and neointimal boundaries were determined by one slide reviewer (A.M.) and verified in a blinded fashion by a second reviewer (C.P.). Lesion size was expressed as the neointima/media ratio. Results for each group were expressed as the mean±SEM. 92% or more of the images were interpretable in each group; the remainder suffered from fixation artifacts and were not analyzed.

Statistical analysis—When appropriate, data from quantitative studies were expressed as the mean±SEM. For multiple treatment groups, a factorial ANOVA followed by Fisher's least significant difference test was applied. Statistical significance was accepted at $p<0.05$.

Results

Figure 1A:
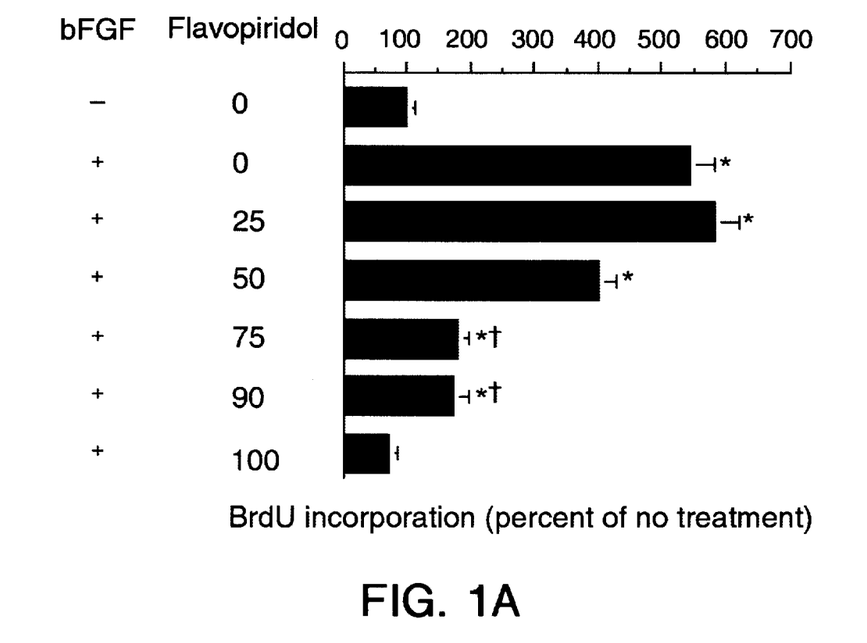

Flavopiridol inhibits HASMC proliferation—On the basis of flavopiridol's ability to inhibit the proliferation of a variety of tumor cell lines, we tested the hypothesis that its use would block the growth of primary culture human SMC. Growth-arrested HASMC were treated with the SMC mitogen bFGF (10 ng/ml) for 24 h in the presence of increasing concentrations of flavopiridol and proliferation was measured by an ELISA-based assay. In comparison with untreated cells, proliferation of bFGF-treated cells was increased 5.4-fold (FIG. 1A). Pretreatment for 1 h with as little as 50 nmol/L flavopiridol significantly decreased HASMC proliferation (to 3.9-fold, $p<0.05$), an effect that was nearly maximal at concentrations of 75 nmol/L. Similar results were obtained using thymidine uptake as an independent measure of DNA synthesis (not shown).

Figure 1B:
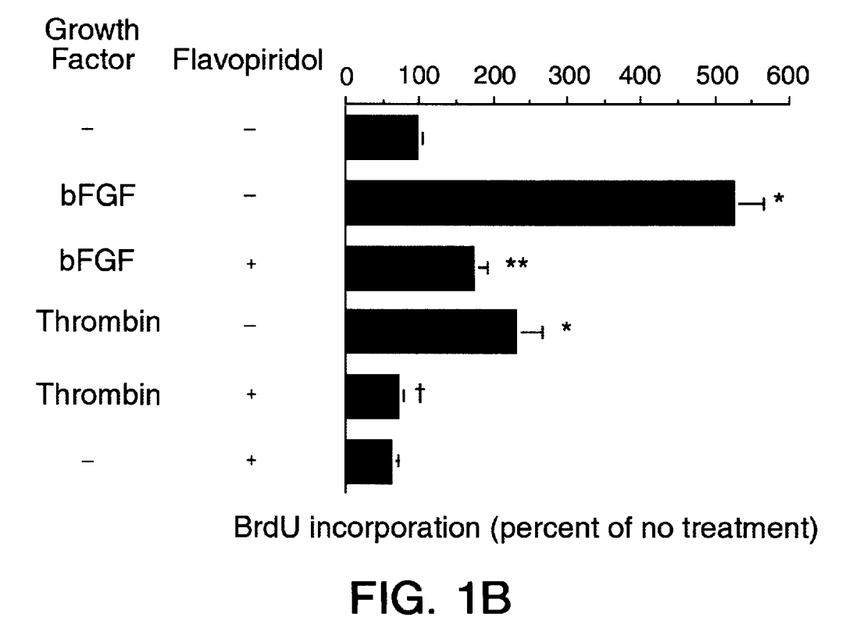
Figure 2:
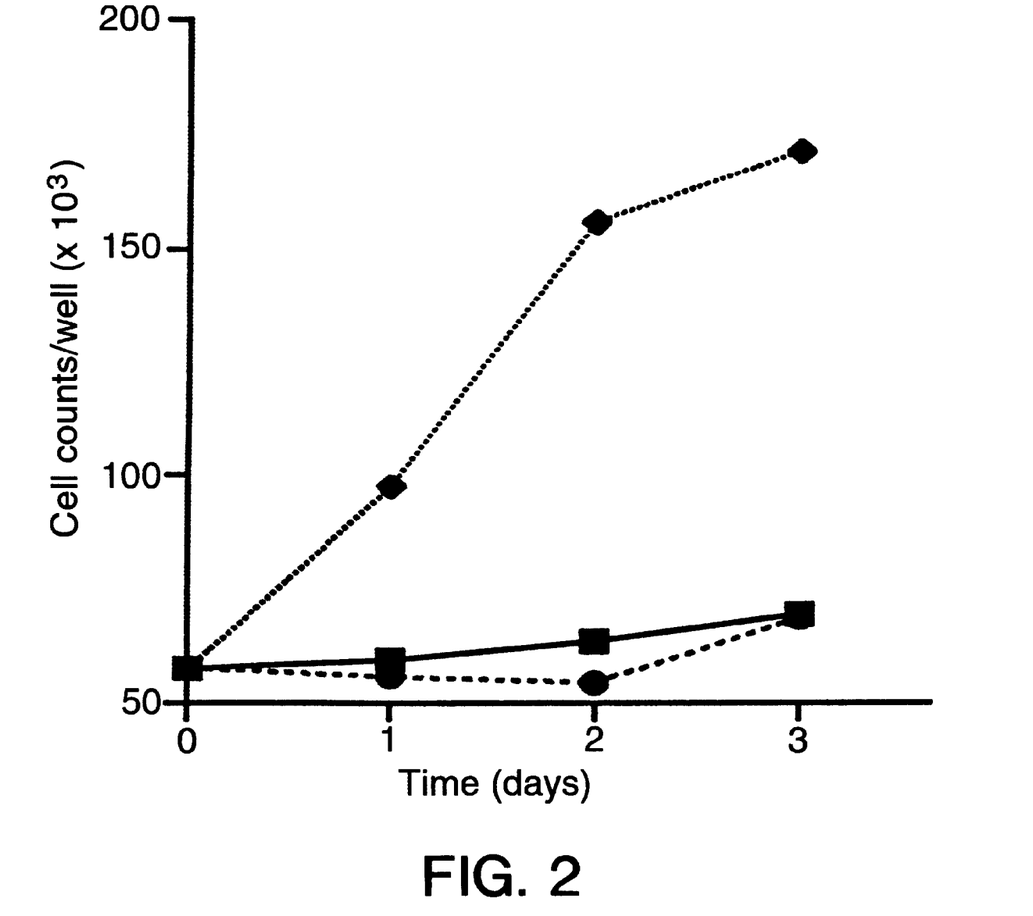

To test the generality of flavopiridol's effects on SMC proliferation, we examined its effect on mitogenesis elicited by thrombin (2 U/ml), which acts through a G protein-coupled receptor, in comparison with bFGF, which stimulates a member of the receptor tyrosine kinase family. Flavopiridol (75 nmol/L) significantly and potently inhibited both bFGF- and thrombin-induced HASMC proliferation (5.4-fold vs. 1.8-fold and 2.4-fold vs. 0.7-fold, respectively, $p<0.05$, FIG. 1B). We performed cell counts to confirm that the effect of flavopiridol on cell cycle progression in HASMC truly reflected changes in proliferation. bFGF (10 ng/ml) induced a 3-fold increase in cell number after three days of treatment (FIG. 2). Similar to the results seen in the ELISA-based assays, flavopiridol (75 nmol/L) efficiently blocked bFGF-induced proliferation.

Figure 3:
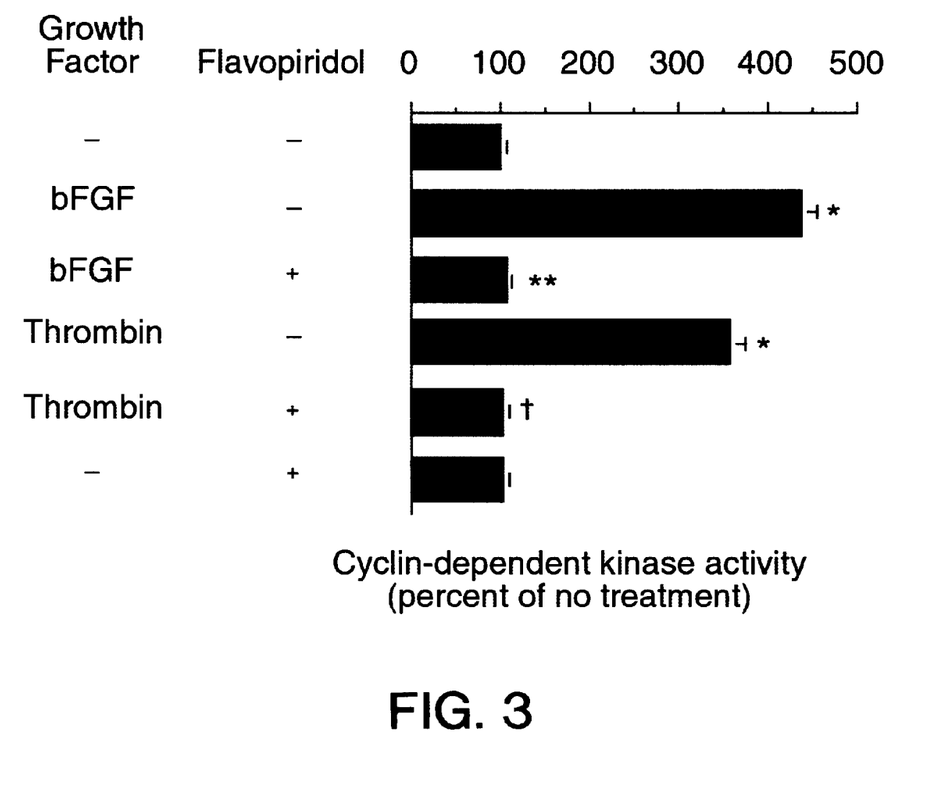

Flavopiridol inhibits Cdk activity and cell cycle-related gene expression in HASMC—To assess the specific effect of flavopiridol on the cell cycle machinery, we measured histone H1 kinase activity in cellular lysates from growth factor-stimulated HASMC. Phosphorylation of histone H1 reflects the activities of $Cdc_2$ and $Cdk_2$[20]. Treatment of HASMC with bFGF and thrombin resulted in 4.4-fold and 3.6-fold increases, respectively, in histone H1 kinase activity (FIG. 3). These increases in cyclin-dependent kinase activity were totally blocked by pretreatment with flavopiridol (75 nmol/L).

By Western blot analysis, we also addressed whether flavopiridol influenced growth factor-induced regulation of cell cycle-related proteins in HASMC. Cyclin $D_1$ is a $G_1$ phase cyclin that is upregulated by growth factor stimulation and is rapidly degraded during withdrawal from the cell cycle[21]. Cyclin D1 protein levels were upregulated 6.3-fold and 3.2-fold, respectively, in response to bFGF and thrombin treatment for 24 h (FIG. 4), an effect which could be completely blocked by pretreatment with flavopiridol. Similarly, increased expression of PCNA, which is synthesized predominantly during S phase in conjunction with DNA replication[22], was also blocked by flavopiridol pretreatment. As a final measure of cell cycle-related proteins, we examined Rb phosphorylation in response to growth factor expression using an antibody that recognizes phosphorylated Rb. Rb is a cell cycle regulator that binds to and inactivates transcription factor E2F when Rb is in the unphosphorylated state[23] and induces SMC growth arrest in vivo[11]. Phosphorylation inactivates Rb and allows progression through S phase to proceed. Analysis of Rb phosphorylation is particularly relevant because Rb is a target of $Cdk_2$ and Cdk4 in vivo. Both thrombin and bFGF induced hyperphosphorylation of Rb, an effect that was inhibited by flavopiridol. Taken together, these results indicate that flavopiridol influences the expression and activity of $G_1$ and S phase-related cell cycle control elements in HASMC in association with its growth-inhibitory effects.

Figure 4:
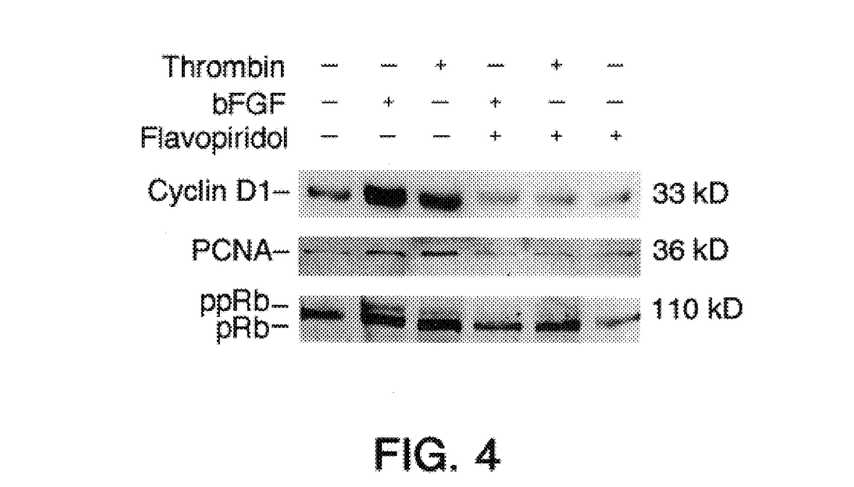
Figure 5:
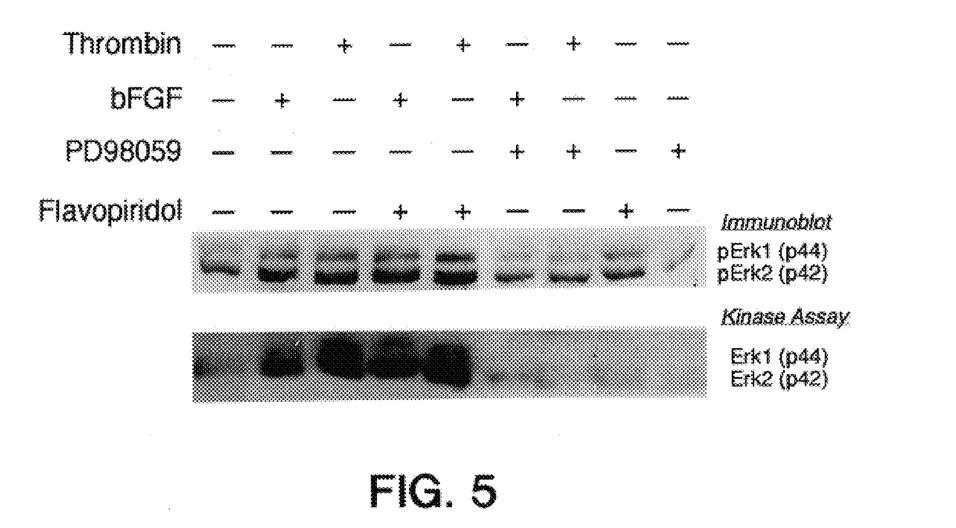

Flavopiridol has no effect on MAP kinase phosphorylation or activity—To ensure that flavopiridol was acting specifically at the level of the cell cycle, rather than non-specifically on upstream kinase pathways, we measured phosphorylation and activity of Erk1 (p44 MAP kinase) and Erk2 (p42 MAP kinase), two members of the MAP kinase family. We chose these kinases because they are immediately upstream of transcriptional events occurring in response to growth stimuli and downstream of a number of critical mitogenic signaling pathways[24]. An intact response by MAP kinases indicates that the upstream mitogenic pathways are also intact. We measured the phosphorylation status of Erk1 and Erk2 with a monoclonal antibody that specifically recognizes the phosphorylated and, hence, activated forms. As a control in these experiments, we used PD98059, a potent and selective inhibitor of MAP kinase activation[25]. Increased amounts of phosphorylated Erk1 and Erk2 were detected after treatment of HASMC with thrombin and bFGF for 30 min, compared with untreated cells (FIG. 5, upper panel). Phosphorylation of Erk1 and Erk2 by both thrombin and bFGF was blocked by pretreatment with PD98059, but not with flavopiridol. To confirm these findings, we measured Erk1 and Erk2 activity by an in-gel kinase assay (FIG. 5, lower panel). Again, we found that Erk1 and Erk2 activities were increased in response to thrombin and bFGF, an effect that was inhibitable by PD98059 but not by flavopiridol. These experiments, in conjunction with those presented in FIGS. 3 and 4, provide evidence that the effects of flavopiridol on HASMC proliferation are due to a specific arrest of the cell cycle machinery by blocking Cdk activity without affecting upstream signaling events.

Figure 6:
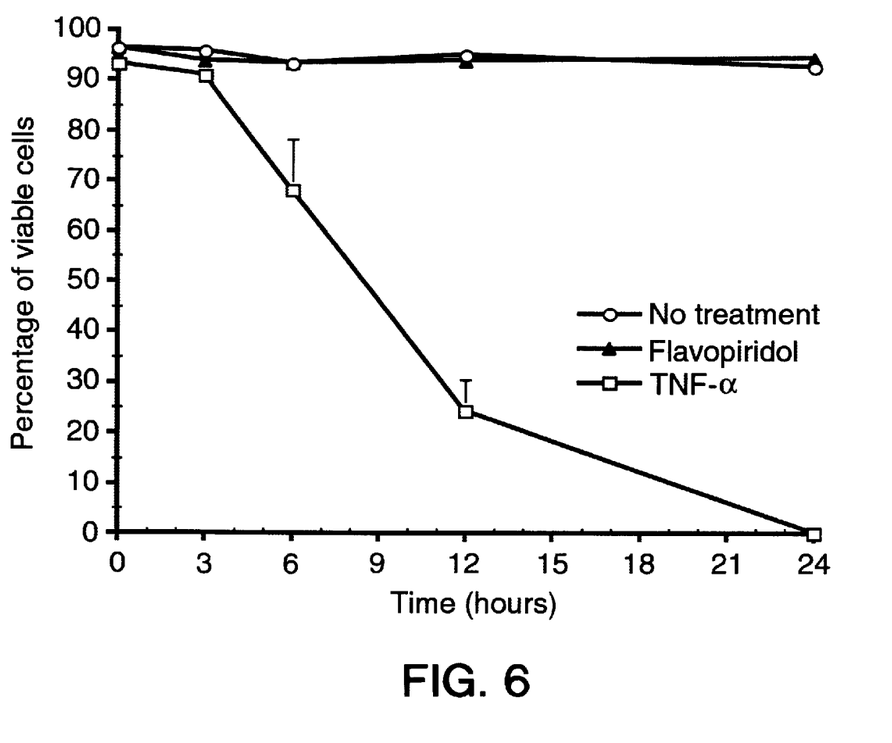
FIG. 6. HASMC viability after treatment with flavopiridol. Quiescent HASMC were treated with flavopiridol (75 nmol/L), TNF-□ (50 ng/ml), or vehicle for the times indicated. Cellular viability was assessed by trypan blue exclusion. Results are expressed as the percentage of viable cells to total cells counted.

Flavopiridol does not decrease HASMC viability— Previous reports of flavopiridol activity in other cell types have demonstrated that, depending on the cell line, flavopiridol may either induce growth arrest without affecting viability, or it may cause apoptosis[16,26-29]. We therefore assessed whether flavopiridol decreased the viability of HASMC by measuring trypan blue exclusion at various time points after treatment. Quiescent HASMC were treated with flavopiridol (75 nmol/L), vehicle, or TNF-□ (50 ng/ml), a cytokine known to induce apoptosis in this cell type[30]. Whereas TNF-□ potently decreased the viability of HASMC, resulting in the death of essentially all cells treated for 24 h, flavopiridol had no such effect (FIG. 6). We have noted that with higher concentrations and longer incubations, some decreases in viability in the presence of flavopiridol may occur (not shown). However, under the conditions tested, flavopiridol primarily induces growth arrest, without affecting SMC viability.

Figure 7:
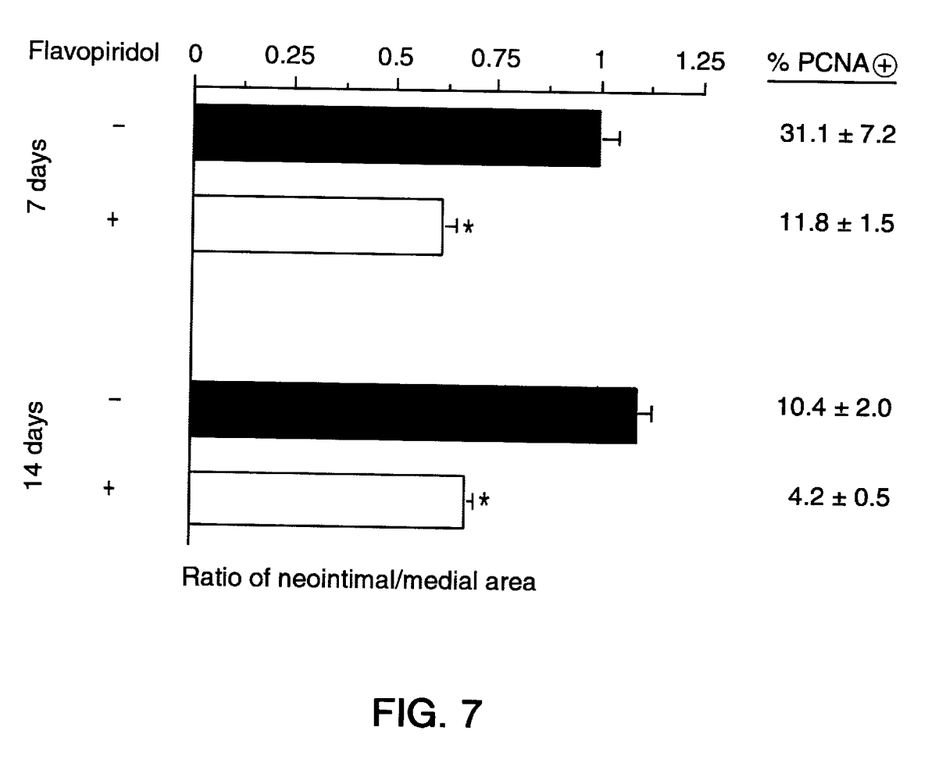
Figure 8A:
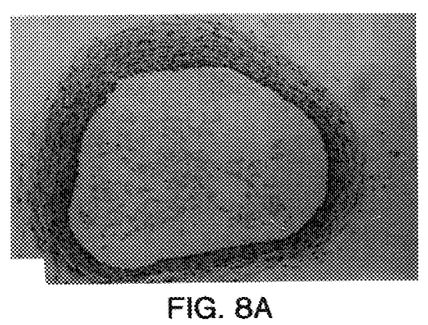
FIG. 8. Histologic sections from rat carotid arteries. Sections are from arteries 7 (panels A and B) and 14 (panels C and D) days after injury. The arteries shown in panels A and C were from rats treated with flavopiridol (5 mg/kg) by gavage; the arteries in panels B and D were from rats treated with vehicle alone. Original magnification, ×100.
Figure 8B:
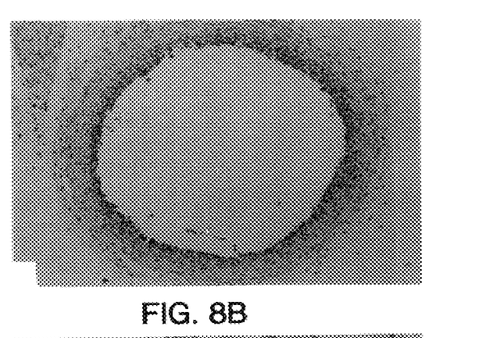
Figure 8C:
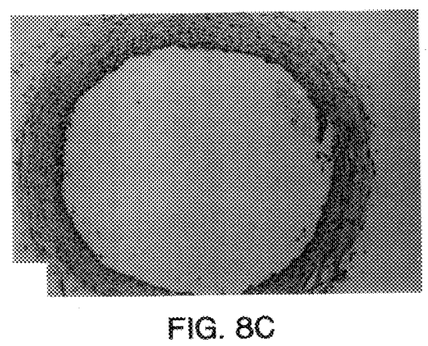
Figure 8D:
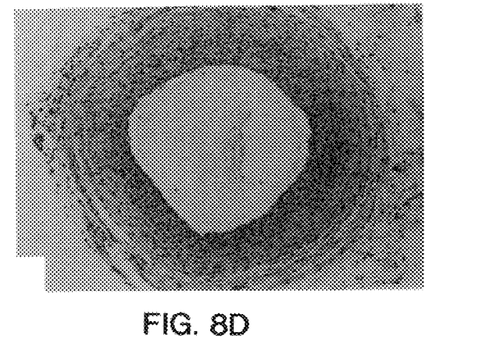
Figure 9A:
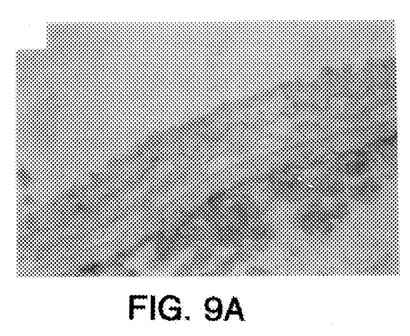
Figure 9B:
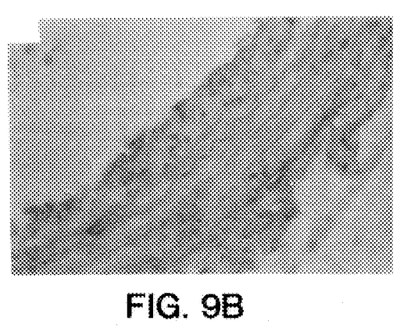
Figure 9C:
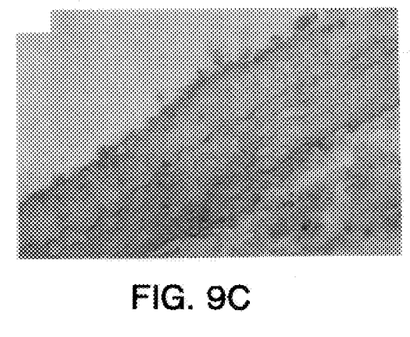
Figure 9D:
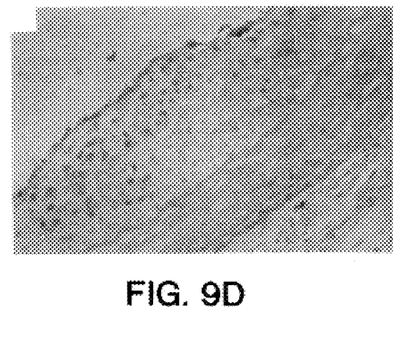

Flavopiridol inhibits smooth muscle cell proliferation and neointimal formation in vivo in a rat carotid injury model of vascular injury—We utilized the well-established rat carotid injury model, in which neointimal lesion formation after catheter-induced injury is critically dependent on SMC proliferation[2,3], to examine whether flavopiridol induces growth arrest of SMC in vivo, as it does in vitro. We administered flavopiridol orally at a dose of 5 mg/kg once daily, beginning on the day of injury and for four days after, since this time period covers the initial induction of $Cdk_2$ and the first wave of SMC proliferation in this model[31, 32]. Mean intimal and medial areas were quantified 7 and 14 days after injury, and neointimal lesion size was expressed as the ratio of the neointimal to the medial area. Twelve animals each were in the treated and untreated groups. The neointima/media ratio at 7 days was 1.00±0.05 in arteries of vehicle-treated rats and 0.65±0.04 in flavopiridol-treated rat arteries, a reduction of 35.0% (FIG. 7). At 14 days, the neointima/media ratio was 1.08±0.04 in vehicle-treated rats and 0.66±0.03 in flavopiridol-treated rats, a reduction of 38.9%. These effects were statistically significant at both time points ($p<0.05$). Representative arterial sections are shown in FIG. 8.

In order to demonstrate directly that flavopiridol inhibited smooth muscle cell proliferation, we stained sections for PCNA expression in representative fields from each artery and determined the percentage of PCNA-positive nuclei in the neointima. At 7 days, 31.1±7.2% of nuclei in injured arteries from untreated rats were PCNA-positive, whereas only 11.8±1.5% of injured arteries in flavopiridol-treated rats were PCNA-positive (FIG. 7; $p<0.05$). At 14 days, PCNA-positive nuclei were present in 10.4±2.0% of neointimal cells from treated, but in only 4.2±0.5% of neointimal cells from untreated, injured rat arteries ($p<0.05$). (PCNA-positive nuclei were rarely seen in uninjured arteries irrespective of treatment.) Similarly, $Cdk_2$-positive cells were much less common in the neointima of flavopiridol-treated rats (FIG. 9, panels A and C), compared with arteries from untreated rats (panels B and D), at both 7 and 14 days after injury.

Discussion

In the present study, we have examined whether the novel Cdk inhibitor, flavopiridol, the most potent and specific inhibitor of Cdks known, is a suitable candidate for inhibiting SMC proliferation in vivo, particularly in the setting of vascular injury. Previous attempts to target the cell cycle machinery therapeutically for the treatment of vascular disease have provided a rationale for the present studies[9-12]; however, methods employed to this end have relied on gene transfer technologies to inhibit cell cycle progression. At present, formidable obstacles prevent the clinical application of these techniques[33]. During the course of our studies, it was reported that CVT-313, a recently identified compound that also has Cdk inhibitory properties but at micromolar concentrations, can also inhibit neointimal formation; however, it was required that CVT-313 be instilled into the carotid artery at the time of injury to produce this effect[34]. In contrast, we show that flavopiridol, when administered orally, can potently inhibit neointimal formation, to a degree comparable with other clinically relevant agents[11,35,36]. The oral activity of flavopiridol makes it virtually unique among agents shown to be active in animal models of vascular injury. Its selectivity, potency, and ease of administration make flavopiridol an excellent candidate for examining the therapeutic benefits of cell cycle inhibition in vivo in human vascular lesions.

We chose to administer flavopiridol orally in a concentration (5 mg/kg) half that which inhibits tumor growth in a nude mouse xenograft model[27]. It is notable that flavopiridol concentrations of 75 nmol/L result in near complete inhibition of SMC proliferation in our studies, whereas median serum concentrations of 425 nmol/L were attained at doses below the toxic threshold in Phase I human studies of refractory carcinoma[17]. Our results suggest that much lower doses of cell cycle inhibitors than those used for neoplasia may be effective in the setting of vascular diseases such as restenosis, with the concomitant benefit of increased tolerability.

Whereas we have demonstrated that flavopiridol induces growth arrest without affecting viability of HASMC in culture, and have shown decreased neointimal formation after flavopiridol treatment in vivo, we cannot be sure that cell cycle arrest is the only factor reducing neointimal formation in carotid lesions. Flavopiridol can induce growth arrest with or without inducing apoptosis, depending on the cell type observed[29]. Interestingly, flavopiridol inhibits apoptosis in PC12 cells that have been terminally differentiated, yet it induces apoptosis in undifferentiated PC12 cells that are proliferating[28]. Although our in vitro experiments were performed under conditions that would mimic the phenotype of SMC prior to injury, it is possible that SMC may respond differently to flavopiridol after injury and may even undergo apoptosis. While the role of apoptosis in vascular lesions is unclear, expression of the Fas ligand in SMC induces apoptosis and blocks neointimal formation in rabbits after balloon injury[37], suggesting that if flavopiridol does indeed induce apoptosis of SMC in vivo, as it does in proliferating PC12 cells, this may be a salutary phenomenon in the context of neointimal formation. Other mechanisms may also contribute to the effects of flavopiridol on lesion formation. For example, antisense oligodeoxynucleotide-mediated cell cycle inhibition improves endothelial function in rabbit vein grafts[38]. Further studies will be needed to address mechanisms of flavopiridol's effects, other than growth arrest, on SMC in vivo.

Given the demonstrated role of SMC proliferation in lesion formation after rat carotid injury[2, 3], it is interesting to note that, despite the profound effects of flavopiridol in vitro, its ability to inhibit neointimal formation (though significant) was more modest under the conditions of our in vivo experiments. We have considered several explanations for this observation. It is unlikely that accelerated SMC proliferation occurs after cessation of flavopiridol, since differences in proliferative indices are sustained as long as 14 days after injury (FIGS. 7 and 9). It is more plausible either that other components of lesion formation, such as SMC migration and extracellular matrix production, still contribute to lesion formation, even in the absence of significant SMC proliferation, or that delivery of flavopiridol once daily is insufficient to arrest proliferation entirely in this model. Recent data indicating that the biological half-life of flavopiridol is as short as 2.5 hrs suggests that the latter hypothesis may be correct; further studies may be able to identify an even more effective dosing regimen[39].

Our results indicate that flavopiridol can inhibit SMC proliferation and, hence, neointimal formation in a well-accepted small animal model of vascular disease. It must be pointed out that the relevance of inhibition of SMC proliferation is controversial in human vascular lesions, and may differ depending on the nature of the lesion and the time at which observations of proliferation are made. The proliferative index of SMC in human atherectomy specimens is remarkably low[40], although these specimens may not reflect proliferative changes at earlier, more critical stages in lesion development. In addition, arterial remodeling independent of neointimal growth may account for a significant proportion of luminal obstruction after angioplasty in humans[42]. In contrast, indices of mitotic activity in SMC are much higher (25% PCNA-positive) in atherectomy specimens from human lesions with in-stent restenosis, consistent with the established role of SMC hyperplasia, but not remodeling, in this process[4]. As stent placement and the clinical problem of in-stent restenosis increases, so will the need for an effective means to arrest SMC hyperplasia and neointimal formation. Since flavopiridol is a potent, orally available drug with specific Cdk-inhibitory activity, and since safe doses of flavopiridol are known in humans, flavopiridol can be considered as a pharmacologic candidate for prevention of in-stent restenosis in humans.

Mehtods and Results: Using cultured human arotic smooth muscle cells, we found that flavopiridol in concentration as low as 75nmol/L resulted in near complete inhibition of basic fibroblast growth factor-and thrombin-induced proliferation. At this dose, flavopiridol inhibited cyclin-dependent kinase activity, as measured by histone $H_1$ phosphorylation, but had no effect on MAP kinase activation. Induction of cell cycle-related proteins cyclin $D_1$, proliferatingcell nuclear antigen, and phosphorylated retinablastoma protein was also blocked by flavopiridol. Flavopiridol had no effect on cellular viability. To test whether flavopiridol had a similar activity in vivo when administered orally, we examined neointimal formation in rat carotid arteries after balloon injury. Flavapiridol (5 mg/kg) administered by gavage reduced neointimal area by 35% and 39% at 7 and 14 days, respectively, after injury.

Conclusions: Flavopiridol inhibits SMC growth in vitro and in vivo. It's oral availability and selectivity for cyclin-dependent kinaeses make it a potential therapeutic tool in the treatment of SMC-rich vascular lesions.

REFERENCES

1. Ross R. The pathogenesis of atherosclerosis: a perspective for the 1990s. *Nature* 1993; 362:801–9.
2. Clowes A W, Reidy M A, Clowes M M. Kinetics of cellular proliferation after arterial injury. *Lab. Invest.* 1983; 49:327–333.
3. Clowes A, Schwartz S. Significance of quiescent smooth muscle migration in the injured rat carotid artery. *Circ. Res.* 1985; 56:139–145.
4. Kearney M, Pieczek A, Haley L, Losordo D W, Andres V, Schainfeld R, Rosenfield K, Isner J M. Histopathology of in-stent restenosis in patients with peripheral artery disease. *Circulation* 1997; 95:1998–2002.
5. Mintz G S, Hoffmann R, Mehran R, Pichard A D, Kent K M, Satler L F, Popma J J, Leon M B. In-stent restenosis: the Washington Hospital Center experience. *Am. J. Cardiol.* 1998; 81:7E–13E.
6. Califf R M. Restenosis: the cost to society. *Am. Heart J.* 1995; 130:680–684.
7. Sherr C J. Mammalian $G_1$ cyclins. *Cell* 1993; 73:1059–1065.
8. Hunter T. Braking the cycle. *Cell* 1993; 75:839–841.
9. Chen D, Krasinski D, Chen D, Sylvester A, Chen J, Nisen P D, Andres V. Downregulation of cyclin-dependent kinase 2 activity and cyclin A promoter activity in vascular smooth muscle cells by $p27^{KIP1}$, an inhibitor of neointima formation in the rat carotid artery. *J. Clin. Invest.* 1997; 99:2334–2341.
10. Chang M W, Barr E, Lu M M, Barton K, Leiden J M. Adenovirus-mediated over-expression of the cyclin/cyclin-dependent kinase inhibitor, p21 inhibits vascular smooth muscle cell proliferation and neointima formation in the rat carotid artery model of balloon angioplasty. *J. Clin. Invest.* 1995; 96:2260–2268.
11. Chang M W, Barr E, Seltzer J, Jiang Y-Q, Nabel E G, Parmacek M S, Leiden J M. Cytostatic gene therapy for vascular proliferative disorders with a constitutively active form of the retinoblastoma gene product. *Science* 1995; 267:518–522.
12. Morishita R, Gibbons G H, Horiuchi M, Ellison K E, Nakajima M, Zhang L, Kaneda Y, Ogihara T, Dzau V J. A gene therapy strategy using a transcription factor decoy of the E2F binding site inhibits smooth muscle proliferation in vivo. *Proc. Natl. Acad. Sci. USA* 1995; 92:5855–5859.
13. Losiewitz M D, Carlson B A, Kaur G, Sausville E A, Worland P J. Potent inhibition of Cdc2 kinase activity by the flavanoid, L86-8275. *Biochem. Biophys. Res. Commun.* 1994; 201:589–595.
14. Carlson B A, Dubay M M, Sausville E A, Brizuela L, Worland P J. Flavopiridol induces $G_1$ arrest with inhibition of cyclin-dependent kinase (CDK) 2 and CDK4 in human breast carcinoma cells. *Canc. Res.* 1996; 56:2973–2978.
15. de Azevedo W F, Mueller-Dieckmann H-J, Schuze-Gahmen U, Worland P J, Sausville E, Kim S-H. Structural basis for specificity and potency of a flavanoid inhibitor of human Cdk2, a cell cycle kinase. *Proc. Natl. Acad. Sci. USA* 1996; 93:2735–2740.
16. Kaur G, Stetler-Stevenson M, Sebers S, Worland P, Sedlacek H, Myers C, Czech J, Naik R, Sausville E. Growth inhibition with reversible cell cycle arrest of carcinoma cells by flavone L86-8275. *J. Natl. Canc. Inst.* 1992; 84:1736–1740.
17. Senderowicz A M, Headlee D, Stinson S, Lush R M, Figg W D, Pluda J, Sausville E A. A Phase I trial of flavopiridol (FLA), a novel cyclin-dependent kinase inhibitor, in patients with refractory neoplasm. *Proc. Am. Soc. Clin. Oncol.* 1997; 16:226a. Abstract.
18. Ruef J, Hu Z Y, Yin L-Y, Wu Y, Hanson S R, Kelly A B, Harker L A, Rao G N, Runge M S, Patterson C. Induction of vascular endothelial growth factor in balloon-injured baboon arteries. *Circ. Res.* 1997; 81:24–33.
19. Ruef J, Rao G N, Li F, Bode C, Patterson C, Bhatnagar A, Runge M S. Induction of rat aortic smooth muscle cell growth by the lipid peroxidation product 4-hydroxy-2-nonenal. *Circulation* 1998; 97:1071–1078.
20. Swank R A, Th'ng J P, Guo X W, Valdez J, Bradbury E M, Gurley L R. Four distinct cyclin-dependent kinases phosphorylate histone $H_1$ at all of its growth related phosphorylation sites. *Biochemistry* 1997; 36:13761–13768.
21. Matsushime H, Roussel M F, Ashmun R A, Sherr C J. Colony-stimulating factor 1 regulates novel cyclins during the $G_1$ phase of the cell cycle. *Cell* 1991; 65:701–713.
22. Bravo R. Synthesis of the nuclear protein (PCNA) and its relationships with DNA replication. *Exp. Cell Res.* 1986; 163:287–293.
23. Ewen M E, Sluss H K, Sherr C J, Matsushime H, Kato J Y, Livingston D M. Functional interaction of the retinoblastoma protein with mammalian D-type cyclins. *Cell* 1993; 7:487–497.

24. Hunter T. Protein kinases and phosphatases: The yin and yang of protein phosphorylation and signaling. *Cell* 1995; 80:225–236.
25. Payne D M, Rossomando A J, Martino P, Erickson A K, Her J-H, Shabanowitz J, Hunt D F, Weber M J, Sturgill T W. Identification of the regulatory phosphorylation sites in pp42/mitogen-activated protein kinase (MAP kinase). *EMBO J.* 1991; 10:885–892.
26. Konig A, Schwartz G K, Mohammad R M, Al-Katib A, Gabrilove J L. The novel cyclin-dependent kinase inhibitor flavopiridol downregulates Bcl-2 and induces growth arrest and apoptosis in chronic B-cell leukemia lines. *Blood* 1997; 90:4307–4312.
27. Drees M, Dengler W A, Roth T, Labonte H, Mayo J, Malspeis L, Grever M, Sausville E A, Fieberg H H. Flavopiridol (L86-8275): Selective antitumor activity in vitro and activity in vivo for prostate carcinoma cells. *Clin. Cancer Res.* 1997; 3:273–279.
28. Park D S, Rarinelli S E, Greene L A. Inhibitors of cyclin-dependent kinases promote survival of post-mitotic neuronally differentiated PC12 cells and sympathetic neurons. *J. Biol. Chem.* 1996; 271:8161–8169.
29. Parker B W, Kaur G, Nieves-Niera W, Taimi M, Kohlhagen G, Shimizu T, Losiewicz M D, Pommier Y, Sausville E A, Senderowicz A M. Early induction of apoptosis in hematopoietic cell lines after exposure to flavopiridol. *Blood* 1998; 91:458–465.
30. Geng Y J, Wu Q, Muszynski M, Hansson G K, Libby P. Apoptosis of vascular smooth muscle cells induced by in vitro stimulation with interferon-gamma, tumor necrosis factor-alpha, and interleukin-1 beta. *Arterioscier. Thromb. Biol.* 1996; 16:19–27.
31. Schwartz S M, deBlois D, O'Brien E R M. The intima: soil for atherosclerosis and restenosis. *Circ. Res.* 1995; 77:445–465.
32. Wei G L, Krasinkski K, Kearney M, Isner J M, Walsh K, Andres V. Temporally and spatially coordinated expression of cell cycle regulatory factors after angioplasty. *Circ. Res.* 1997; 80:418–426.
33. de Young M B, Dichek D A. Gene therapy for restenosis. *Circ. Res.* 1997; 82:306–313.
34. Brooks E E, Gray N S, Joly A, Kerwar S S, Lum R, Mackman R L, Norman T C, Rosete J, Rowe. M, Schow S R, Schultz T G, Wang X, Wick M M, Shiffman D. CVT-313, a specific and potent inhibitor of CDK2 that prevents neointimal formation. *J. Biol. Chem.* 1997; 272:299207–29911.
35. Sirois M G, Simons M, Edelman E R. Antisense oligonucleotide inhibition of PDGFR-b receptor subunit expression directs suppression of intimal thickening. *Circulation* 1997; 95:669–676.
36. Rade J J, Schulick A H, Virmani R, Dichek D A. Local adenoviral-mediated expression of recombinant hirudin reduces neointima formation after arterial injury. *Nature Med.* 1996; 2:293–298.
37. Sata M, Perlman H, Muruve D A, Silver M, Ikebe M, Libermann T A, Oettgen P, Walsh K. Fas ligand gene transfer to the vessel wall inhibits neointima formation and overrides the adenovirus-mediated T cell response. *Proc. Natl. Acad. Sci. USA* 1998; 95:1213–1217.
38. Mann M J, Gibbons G H, Tsao P S, von der Leyen H E, Cooke J P, Buitrago R, Kernoff R, Dzau V J. Cell cycle inhibition preserves endothelial function in genetically engineered rabbit vein grafts. *J. Clin. Invest.* 1997; 99:1295–1301.
39. Arguello F, Alexander M, Sterry J A, Tudor G, Smith E M, Kalavar N T, Greene J F, Koss W, Morgan C D, Stinson S F, Siford T J, Alvord W G, Klabansky R L, Sausville E A. Flavopiridol induces apoptosis of normal lymphoid cells, causes immunosuppression, and has potent antitumor activity in vivo against human leukemia and lymphoma xenografts. *Blood* 1998; 91:2482–2490.
40. O'Brien E R, Alpers C E, Stewart D K, Ferguson M, Tran N, Gordon D, Benditt E P, Hinohara T, Simpson J B, Schwartz S M. Proliferation in primary and restenotic coronary atherectomy tissue: implications for antiproliferative therapy. *Circ. Res.* 1993; 73:223–231.
41. Mintz G S, Popma J J, Pichard A D, Kent K M, Satler L R, Wong S C, Hong M D, Kovach J A, Leon M B. Arterial remodeling after coronary angioplasty: a serial intravascular ultrasound study. *Circulation* 1996; 94:35–43.

What is claimed is:

1. A method of inhibiting smooth muscle cell proliferation comprising administering to a patient an effective amount of a compound of the formula I, which is less than 70% if the dosage to control tumor growth, Formula I wherein
R$_1$ is hydrogen, alkyl having 1 to 6 carbon atoms, aryl-C$_1$-C$_4$-alkyl; C$_1$-C$_6$-alkyl substituted by halogen, hydroxy, or carboxy; C$_3$-C6-cycloalkyl, pyridyl, thienyl, C$_3$-C$_6$-cycloalkyl-C$_1$-C$_4$-alkyl, C$_2$-C$_6$-alkenyl, C$_2$-C$_6$-alkynyl, phenyl; phenyl, mono- or polysubstituted by halogen, C$_1$-C$_4$-alkyl, C$_1$-C$_4$-alkoxy, hydroxyl, carboxyl, COO-alkyl, CONH$_2$, CONH-alkyl, CON(alkyl)$_2$, nitro, trifluoromethyl, amino, C$_1$-C$_4$-alkylamino, di-C$_1$-C$_4$-alkylamino, or phenyl; naphthyl, carboxyl, —CHO, COO-C$_1$-C$_4$-alkyl, a primary amino, alkylamino, aralkylamino, dialkylamino, amido, arylamino, diarylamino, or —CH$_2$O-C$_1$-C$_4$-alkyl;

R$_2$ is hydrogen, alkyl having 1 to 6 carbon atoms, aryl, nitro, amino, di-C$_1$-C$_4$-alkylamino, a halogen, hydroxyl, alkoxy, —COOH, —COO-C$_1$-C$_4$-alkyl, —CHO, —CH$_2$OH or —CH$_2$O-C$_1$-C$_4$-alkyl;

R$_3$ is hydrogen, C$_1$-C$_4$-alkyl; C$_1$-C$_4$-alkyl substituted by halogen, hydroxy or carboxy; hydroxyl, carboxyl, nitro, amino, C$_1$-C$_4$-alkylamino, di-C$_1$-C$_4$-alkylamino, halogen, —O-alkyl-C(O)-alkyl, —CHO, —CH$_2$OH, —CH$_2$O-C$_1$-C$_4$-alkyl or R$_2$N—C(O)—O—, wherein R is H, C$_1$-C$_6$-alkyl, cycloalkyl; or —O-alkyl-C(O)-alkyl or aryl;

R$_4$ is hydrogen, hydroxyl C$_1$-C$_4$-alkoxy, C$_1$-C$_4$-alkanoyloxy, C$_1$-C$_4$-alkoxycarbonyl, aryloxy, amino, C$_1$-C$_4$-alkylamino, di-C$_1$-C$_4$-alkylamino, or

R'$_2$—N—C(O)—O— wherein R' is H, C$_1$-C$_6$-alkyl, cycloalkyl or aryl;

R$_5$ is hydrogen, C$_1$-C$_6$-alkyl, aryl-C$_1$-C$_4$ alkyl, C$_3$-C$_6$-cycloalkyl, C$_3$-C$_6$-cycloalkyl-C$_1$-C$_4$-alkyl, alkylamino, $C_1$–$C_4$-alkanoyl, —C(O)—O-$C_1$–$C_4$-alkyl or aroyl, where the aryl group in $R_1$, $R_2$, $R_3$, $R_4$, and $R_5$ is unsubstituted phenyl or phenyl that is mono or polysubstituted by halogen, $C_1$–$C_4$-alkyl, $C_1$–$C_4$-alkoxy, hydroxyl, carboxyl, COO-alkyl, $CONH_2$, CONH-alkyl, $CON(alkyl)_2$, nitro, trifluoromethyl, amino, $C_1$–$C_4$-alkylamino, di-$C_1$–$C_4$-alkylamino or phenyl; m is an integer between 0 and 3 and n is 1, or a pharmacologically acceptable acid addition salt thereof.

2. The method of claim 1, wherein the effective amount of a compound of the formula I is less than 60% of the dosage to control tumor growth.

3. The method of claim 2, wherein the effective amount of a compound of the formula I is less than 50% of the dosage to control tumor growth.

4. The method of claim 1, wherein the compound is a compound of formula Ia compounds of the formula Ia, is less than which is less than 70% of the dosage to control tumor growth, Formula Ia in which $R_1$ is hydrogen, $C_1$–$C_3$-alkyl, naphthyl, phenyl; phenyl mono- or polysubstituted by halogen, $C_1$–$C_4$-alkyl, $C_1$–$C_4$-alkoxy, hydroxyl, carboxyl, COO-alkyl, $CONH_2$, CONH-alkyl, $CON(alkyl)_2$, nitro, trifluoromethyl, amino, $C_1$–$C_4$-alkylamino, di-$C_1$–$C_4$-alkylamino, or phenyl; pyridyl, or thienyl;

$R_2$ is hydrogen or $C_1$–$C_3$-alkyl;

$R_5$ is $C_1$–$C_3$-alkyl, $C_3$–$C_5$-cycloalkyl, or $C_3$–$C_5$-cycloalkyl-$C_1$–$C_4$-alkyl.

5. The method of claim 4, wherein the substituents of formula la have the following meanings $R_1$ is phenyl, thienyl, pyridyl, chlorophenyl, dichlorophenyl, methylphenyl, aminophenyl, bromophenyl, hydroxyphenyl or naphthyl;

$R_2$ is hydrogen and $R_5$ is methyl.

6. The method of claim 5, in which the compound is (−)-cis,-5,7-dihydroxy-2-) (2-chlorophenyl)-8-[4-(3-hydroxy-1-methyl)-piperidinyl]-4H-benzopyran-4-one (Flavopiridol).

7. The method of claim 4, wherein the effective amount of a compound of the formula Ia is less than 60% of the dosage to control tumor growth.

8. The method of claim 7, wherein the substituents of formula Ia have the following meanings $R_1$ is phenyl, thienyl, pyridyl, cholorophenyl, dichlorophenyl, methylphenyl, aminophenyl, bromophenyl, hydroxyphenyl or naphthyl;

$R_2$ is hydrogen and $R_5$ is methyl.

9. The method of claim 8, in which the compound is (−)-cis,-5,7-dihydroxy-2-) (2-chlorophenyl)-8-[4-(3-hydroxy-1-methyl)-piperidinyl]-4H-benzopyran-4-one (Flavopiridol).

10. The method of claim 8, wherein the effective amount of a compound of the formula Ia is less than 50% of the dosage to control tumor growth.

11. The method of claim 11, wherein the substituents of formula Ia have the following meanings $R_1$ is phenyl, thienyl, pyridyl, chlorophenyl, dichlorophenyl, methylphenyl, aminophenyl, bromophenyl, hydroxyphenyl or naphthyl;

$R_2$ is hydrogen and $R_5$ is methyl.

12. The method of claim 11, in which the compound is (−)-cis,-5,7-dihydroxy-2-) (2-chlorophenyl)-8-[4-(3-hydroxy-1-methyl)-piperidinyl]-4H-benzopyran-4-one (Flavopiridol).

13. The method of claims 1 to 12, wherein the administration is for treatment of smooth muscle cell-rich vascular lesions.

14. The method of claims 1 to 12, wherein the administration is for treatment of lesions after balloon injury.

15. The method of claims 1 to 12, wherein the administration is for treatment after stent implantation.

* * * * *